United States Patent
Pilpel et al.

(10) Patent No.: US 9,814,765 B2
(45) Date of Patent: Nov. 14, 2017

(54) ONE COMPONENT FIBRIN GLUE COMPRISING ZYMOGENS

(71) Applicants: Omrix Biopharmaceuticals Ltd., Rehovot (IL); Ethicon, Inc., Somerville, NJ (US)

(72) Inventors: Yair Pilpel, Rehovot (IL); Ashley Deanglis, Skillman, NJ (US); Yuri Zherdev, Rehovot (IL); Sivan Doron, Moshav Arugot (IL); Anne Gorman, Hightstown, NJ (US); Israel Nur, Moshav Timmorim (IL)

(73) Assignees: Ethicon, Inc., Somerville, NJ (US); Omrix Biopharmaeuticals Ltd., Rehovot (IL)

( * ) Notice: Subject to any disclaimer, the term of this patent is extended or adjusted under 35 U.S.C. 154(b) by 43 days.

(21) Appl. No.: 14/560,089

(22) Filed: Dec. 4, 2014

(65) Prior Publication Data

US 2015/0174215 A1    Jun. 25, 2015

Related U.S. Application Data

(60) Provisional application No. 61/920,656, filed on Dec. 24, 2013.

(30) Foreign Application Priority Data

Dec. 24, 2013   (IL) .......................................... 230150

(51) Int. Cl.

| A61K 38/48 | (2006.01) |
| A61K 38/36 | (2006.01) |
| A61K 31/194 | (2006.01) |
| A61K 31/198 | (2006.01) |
| A61K 38/17 | (2006.01) |
| A61K 33/14 | (2006.01) |
| A61L 24/00 | (2006.01) |
| A61L 24/10 | (2006.01) |

(52) U.S. Cl.
CPC ........ *A61K 38/4846* (2013.01); *A61K 31/194* (2013.01); *A61K 31/198* (2013.01); *A61K 33/14* (2013.01); *A61K 38/1767* (2013.01); *A61K 38/36* (2013.01); *A61K 38/363* (2013.01); *A61K 38/4833* (2013.01); *A61L 24/0015* (2013.01); *A61L 24/106* (2013.01); *A61L 2300/254* (2013.01); *A61L 2300/418* (2013.01); *C12Y 304/21005* (2013.01); *C12Y 304/21006* (2013.01); *C12Y 304/21021* (2013.01); *C12Y 304/21022* (2013.01)

(58) Field of Classification Search
None
See application file for complete search history.

(56) References Cited

U.S. PATENT DOCUMENTS

| 5,219,328 | A | 6/1993 | Morse et al. |
| 5,318,524 | A | 6/1994 | Morse et al. |
| 5,750,657 | A | 5/1998 | Edwardson et al. |
| 5,792,835 | A | 8/1998 | Tse et al. |
| 5,985,315 | A * | 11/1999 | Patat ..................... A61L 24/106 424/443 |
| 6,121,232 | A | 9/2000 | Nur et al. |
| 6,262,236 | B1 | 7/2001 | Edwardson et al. |
| 6,268,483 | B1 | 7/2001 | Edwardson et al. |
| 6,500,427 | B1 | 12/2002 | Heimburger et al. |
| 7,125,569 | B2 | 10/2006 | Nur et al. |
| 8,367,802 | B2 | 2/2013 | Falus et al. |
| 2009/0123453 | A1 * | 5/2009 | Eibl ....................... A61K 38/36 424/94.64 |
| 2013/0149292 | A1 | 6/2013 | Chtourou |

FOREIGN PATENT DOCUMENTS

| EP | 1390485 | 10/2006 |
| WO | WO 93/05822 | 4/1993 |
| WO | WO 1997/029792 | 8/1997 |
| WO | WO 98/33533 | 8/1998 |
| WO | WO 02095019 | 11/2002 |
| WO | WO 2008/121330 | 10/2008 |
| WO | WO 2012/045569 | 4/2012 |

OTHER PUBLICATIONS

Dickneite, G. et al. 'A comparison of fibrin sealants in relation to their in vitro and in vivo properties' Thrombosis Res (2003) vol. 112 pp. 73-82.
Raccuia, J.S. et al., 'Comparative Efficacy of Topical Hemostatic Agents in a Rat Kidney Model' Am J Surg. (1992) vol. 163, No. 2 pp. 234-238.
Tabélé, C. et al. 'Organic Glues or Fibrin Glues from Pooled Plasma: Efficacy, Safety and Potential as Scaffold Delivery Systems' J Pharm Pharmaceut Sci (2012) vol. 15, No. 1 pp. 124-140.
International Preliminary Report on Patentability re: PCT/IL2014/000062 dated Jun. 28, 2016.
International Search Report re: PCT/IL2014/000062 dated Apr. 9, 2015.

* cited by examiner

*Primary Examiner* — Michelle F Paguio Frising
(74) *Attorney, Agent, or Firm* — David R. Crichton

(57) ABSTRACT

Provided herein is a single component sealant formulation (e.g. in a liquid form), methods for its preparation, and use. The formulation includes fibrinogen; vitamin K-dependent clotting zymogens comprising at least Factor II (FII) and Factor X (FX).

32 Claims, 5 Drawing Sheets

ONE COMPONENT FIBRIN GLUE COMPRISING ZYMOGENS

FIELD OF THE INVENTION

Provided herein is a single component sealant formulation e.g. in a liquid form, methods for its preparation, and methods of use thereof.

BACKGROUND

Fibrin sealants, also known as fibrin glue, have been in use in the clinic for decades (see, for example, Tabélé, et al. J Pharm Pharmaceut Sci 2012, 15:124-140; Dickneite, G et al. Thrombosis Res 2003, 112:73-82). Oftentimes, fibrin sealant consist of two liquid components, a fibrinogen comprising component and a thrombin comprising component, which are stored frozen due to their inherent instability. Sometimes fibrin sealant products consist of two freeze dried components, which require reconstitution immediately prior to use and delivery by a conjoined syringe or other double-barreled delivery device. Freeze dried formulations are typically stable, but the fibrinogen component is difficult to reconstitute.

A fibrin sealant clot is formed by enzymatic reactions involving fibrinogen, thrombin and Factor XIII. The thrombin converts the fibrinogen to fibrin by enzymatic action at a rate determined by the concentration of thrombin. Factor XIII, an enzyme of the blood coagulation system, cross-links and stabilizes the fibrin clot. This process bypasses most of the steps of normal coagulation and mimics its last phase. Some manufacturers add anti-proteolytic agents to the fibrin glue formulation (e.g. as described in WO93/05822) or specifically remove the plasminogen in order to stop or delay fibrinolysis (e.g. as described in U.S. Pat. Nos. 5,792,835 and 7,125,569).

The thrombin component contains the enzyme thrombin, which is a serine protease, and can be from human or animal (e.g. bovine or porcine) origin or recombinantly produced. The fibrinogen component can be from human or animal origin or recombinantly produced. Upon mixing the two-component solutions, thrombin cleaves fibrinogen thus allowing the latter to generate fibrin polymers/sealant.

Thrombin displays high specificity toward fibrinogen and cleaves a defined sequence in the fibrinogen molecule, however, at very high concentrations thrombin can undergo auto-proteolysis. The auto-proteolytic properties of thrombin may result in reduced activity and instability of the thrombin component of fibrin sealant.

Background art includes U.S. Pat. Nos. 5,219,328; 5,318,524; 8,367,802; 6,500,427; 5,750,657; 6,262,236; 6,268,483; and US Patent Application Publication No. 2013/0149292.

SUMMARY OF THE INVENTION

Provided herein are single component, stable sealant formulations, methods of manufacture and methods of use, which eliminate the cumbersome steps involved in manufacturing, preparing and/or using the known sealant formulations.

In one aspect, provided herein is a sealant formulation comprising an effective amount of fibrinogen, vitamin K-dependent clotting zymogens comprising at least Factor II (FII), and Factor X (FX), and at least one reversible inhibitor of at least one of the vitamin K-dependent clotting zymogen; wherein the formulation is free of an added irreversible thrombin inhibitor.

In another aspect, provided herein is a calcium-free sealant formulation comprising fibrinogen and vitamin K-dependent clotting zymogens comprising at least Factor II and Factor X.

The term "effective amount" for fibrinogen, vitamin K-dependent clotting zymogens and the reversible inhibitor are such that, effectively, little or no premature activation (e.g. coagulation, clotting and/or conversion from zymogen to an active enzyme) takes place, yet the formulation spontaneously coagulates and forms a sealant upon dilution, neutralization, blockage and/or removal of the reversible inhibitor. For example spontaneous coagulation and sealant formation may occur by contact with a bleeding surface, following small molecule exchange, and/or addition of an activator e.g. free calcium.

In some embodiments, the formulation further comprises Factor V (FV).

In some embodiments, the vitamin K-dependent clotting zymogens further comprise Factor IX (FIX).

In some embodiments, the vitamin K-dependent clotting zymogens further comprise Factor VII (FVII).

In some embodiments, Factor X, Factor VII, and/or Factor IX are, at least partially, in their active form.

In some embodiments, the formulation is in liquid form. In some embodiments, the formulation comprises a pharmaceutically acceptable carrier. The liquid formulation exhibits extended stability and remains stable for at least 14 days at an ambient temperature selected from the group consisting of about 2, 3, 4, 5, 6, 7, and 8° C. In some embodiments, the liquid formulation remains stable for about 30, 35, 45 days, 60 days and up to 90 days or more, at a temperature of about 2° C. to 8° C. "Ambient temperature" is the temperature in the surroundings where the sealant formulation is kept.

In some embodiments, the liquid formulation is stable for about or at least 7 days at an ambient temperature in a range of about 2° C. and up to room temperature.

In certain embodiments the liquid formulation is stable for about 30 days at room temperature.

"Room temperature" typically refers to a temperature of about 20° C. to 25° C.

The liquid formulation can be an aqueous liquid formulation.

Stability can be determined by observing minimal or absence of spontaneous clotting in the formulation e.g. the formulation does not show or have spontaneous clotting in the absence of an activator, such as free calcium, and retains its clotting activity level upon exposure to calcium. The clotting activity level or capability of the formulation to form a sealant can be determined in-vitro and/or in-vivo. Stability can also be determined by measuring and observing the presence of minimal or absence of fibrin formation in the shelf-ready aqueous formulation.

Fibrin polymerization or clotting can be measured, for example, by measuring migration length on a slanted surface (or drop test model) or by any other method known in the art. Full polymerization can be assessed by cessation of flow of the liquid formulation upon inversion. Rapid polymerization can be measured using a Stat4 clotting analyzer Stago Diagnostics or similar coagulometer.

The term "activator" refers to an agent that can initiate, facilitate and/or accelerate the conversion of a zymogen into an active enzyme. The term "activator" herein is interchangeable with the term "initiator".

In one embodiment, the source of the vitamin K-dependent clotting zymogens is Prothrombin-Proconvertin-Stuart Factor-Antihemophilic Factor B (PPSB) and/or a three-factor or four-factor Prothrombin Complex Concentrate (PCC).

In some embodiments, PPSB includes Factors II, VII, IX and X.

In some embodiments, PCC includes Factors II, IX and X (three-factor PCC) and may further include Factor VII (four-factor PCC).

In various embodiments, vitamin K-dependent clotting zymogens is a concentrate of vitamin K-dependent clotting zymogens comprising at least FII and FX, concentrated by about 2-50 fold compared to the concentration of these zymogens in plasma, as normalized to Factor II. The concentrate may be concentrated about 5 to about 40 fold, about 10 fold or about 20 fold.

In various embodiments, vitamin K-dependent clotting zymogens is a PPSB concentrate, or concentrated vitamin K-dependent clotting zymogens comprising at least FII, FIX and FX, concentrated by about 2-50 fold compared to the concentration of these zymogens in plasma, as normalized to Factor II. The PPSB concentrate may be concentrated about 5 to about 40 fold, about 10 fold or about 20 fold.

In some embodiments, the fibrinogen is present in the formulation in an effective amount of about 1 to 2 mg/ml, 1 to 110 mg/ml, 10 to 110 mg/ml such as about 40 mg/ml to 70 mg/ml.

In one embodiment, the ratio of the active components: fibrinogen, vitamin K-dependent clotting zymogens, and the reversible inhibitor of at least one of the vitamin K-dependent clotting zymogens, are such that, effectively, little or no premature activation (e.g. coagulation, clotting and/or conversion from zymogen to an active enzyme) takes place, yet the formulation spontaneously coagulates and forms a sealant upon dilution, removal of the reversible inhibitor, blockage and/or neutralize of the inhibitor e.g. by contact with a bleeding surface and/or following small molecule exchange and/or addition of an activator e.g. free calcium.

"A reversible inhibitor of a vitamin K-dependent clotting zymogen" is an agent which effectively prevents or reduces premature activation (e.g. coagulation, clotting and/or conversion from a zymogen to an active enzyme).

In some embodiments, the formulation is free of added thrombin. Accordingly, there is no requirement for a thrombin inhibitor and the formulation is free of added irreversible thrombin inhibitor or is essentially free of an irreversible thrombin inhibitor. An irreversible thrombin inhibitor comprises a group of molecules that bind thrombin covalently or with a very high affinity (e.g. at a picomolar level) e.g. hirudin, and/or destroy a functional group on thrombin or render the thrombin inactive. For example hirudin and antithrombin III are considered herein as examples of such irreversible thrombin inhibitors. In some embodiments, the formulation is free of hirudin. In one embodiment, the formulation is free of antithrombin III.

The term "free of added" in connection with the terms "free of added thrombin" and "free of added irreversible thrombin inhibitor" means that the formulation is not supplemented with thrombin or irreversible thrombin inhibitor. However, it should be noted that the formulation may comprise low amounts of thrombin (e.g. less than 1 IU/ml formulation) and/or irreversible thrombin inhibitor (e.g. less than 5 µM) originally present in the formulation and/or thrombin spontaneously formed in the formulation.

The formulation includes at least one reversible inhibitor of at least one of the vitamin K-dependent clotting zymogens. Such inhibitor is an agent that can substantially prevent initiation and/or delays the conversion of a zymogen into an active enzyme. The inhibitor can be selected from heparin, a calcium chelator, a reversible serine protease active site inhibitor and a combination of such inhibitors.

Typically, a reversible inhibitor relates to a low affinity inhibitor having no permanent effect on protein activity. Therefore, typically dilution will remove the inhibitory effect.

At least one vitamin K-dependent clotting zymogen reversible inhibitor may be heparin. The vitamin K-dependent clotting zymogen reversible inhibitor which inhibits generation of an active enzyme may be a calcium chelator, for example a citrate ion, EDTA, EGTA, oxalate or a combination of such calcium chelators.

In some embodiments, the calcium chelator is a citrate ion, for example provided by sodium citrate. The formulation may include from about 1 mM to about 50 mM sodium citrate, or from about 5 mM to about 25 mM sodium citrate. In some embodiments, the calcium chelator is EDTA and/or EGTA. The formulation may include from about 0.1 mM to about 2.5 mM EDTA and/or EGTA. In some embodiments, the calcium chelator is oxalate. In some embodiments, the formulation includes a combination of a citrate ion, oxalate and EDTA and/or EGTA, for example EDTA and a citrate ion provided by sodium citrate. In some embodiments, the formulation comprises from about 0.1 mM to about 2.5 mM EDTA and/or EGTA.

In some embodiments, the at least one vitamin K-dependent clotting zymogen reversible inhibitor is a serine protease active site inhibitor, for example arginine, lysine, benzamidine or a combination of such serine protease active site inhibitors. The formulation may include, for example, arginine in an amount from about 0.1% to about 5% (w/v), about 0.5% to about 4% (w/v) arginine, or about 1%, 1.5%, 2%, 2.5%, 3%, 3.5%, or 4% (w/v) arginine.

In some embodiments, the ratio of vitamin K-dependent clotting zymogens (U), including PPSB, vitamin K-dependent clotting zymogens comprising at least FII, FIX and FX, or PCC, to fibrinogen (mg clottable protein) is about 0.01 to about 1.0, as normalized to Factor IX or Factor II. In some embodiments, the ratio is about 0.05 to about 0.2, or about 0.1 to about 0.2.

In some embodiments, the ratio of vitamin K-dependent clotting zymogens (U), including PPSB, vitamin K-dependent clotting zymogens comprising at least FII, and FX, or PCC, to fibrinogen (mg clottable protein) is about 0.01 to about 1.0, as normalized to Factor II. In some embodiments, the ratio is about 0.05 to about 0.2, or about 0.1 to about 0.2.

The formulation is preferably sterile and free from pathogens, for example by pasteurization and/or filtration.

The formulations disclosed hereinabove are useful in, for example, hemostasis, healing, and/or surgery, including, without limitation, graft fixation, wound healing and sealing of anastomosis sites. The formulation can also be used in plastic surgery, for example, abdominoplasty; skin and internal organ graft fixation; tissue healing; burn treatment; and/or attenuating wound bleeding. Furthermore, the formulation is useful for dura sealing, for example in cranial or spinal surgery.

Accordingly, in one aspect, provided is a method of providing hemostatic treatment; graft fixation, wound healing and/or anastomosis, to a surface in a subject, comprising applying to the surface a formulation according to the invention. The method includes, without limitations, abdominoplasty; tissue healing; burn treatment; and dura sealing. The subject may be a human subject.

In another aspect, provided is a formulation according to the invention for use in healing, hemostasis and/or surgery. The uses include, without limitation, graft fixation; wound healing; anastomosis; abdominoplasty; tissue healing; burn treatment; and dura sealing.

In another aspect, provided herein is a method for preparing a sealant at a surface comprising:
a) providing a formulation according to the invention; and
b) applying the formulation to the surface under conditions which facilitate fibrin polymerization at the surface.

The surface can be a bleeding or non-bleeding surface in a subject. The surface may also be for example, a bodily surface, an external or internal body organ, a blood vessel or a graft tissue or organ.

In some embodiments, the conditions described in the above method involve applying the formulation directly to a bleeding or non-bleeding surface in a subject.

Several conditions of activation are disclosed. For example, the mixture of PPSB and fibrinogen may be applied directly onto a bleeding site in which case the inhibitors are diluted and the concentrated zymogens and fibrinogen function in order to rapidly bring about hemostasis.

In some embodiments, the conditions involve (i) removing, diluting, blocking and/or neutralize the reversible inhibitor of at least one of the vitamin K-dependent clotting zymogens and/or (ii) adding a small molecule activator of at least one of the vitamin K-dependent clotting zymogens.

The small molecule activator may be a phospholipid or a cation, for example a calcium cation or other divalent cations such as magnesium, iron or zinc or combinations thereof. In some embodiments, the cation is a calcium cation, provided by $CaCl_2$.

In some embodiments, the small molecule activator is a phospholipid such as phosphatidylserine, phosphatidylcholine, phosphatidylinositol or phosphatidylethanolamine A small molecule activator or reversible inhibitor has a molecular weight of up to 1 kilodalton.

In various embodiments, the step of removing or diluting the inhibitor of at least one of the vitamin K-dependent clotting zymogens is carried out by passing the formulation through a small molecule exchange device e.g. a column prior to or during application to the surface of a subject.

Typically, small molecule exchange is the replacement of one set of small molecules with another set. Oftentimes, the resin in the column is pre-equilibrated with the small molecules that are desired in the final formulation and/or small molecules that facilitate and/or accelerate the conversion of a zymogen into an active enzyme. The resin beads are typically porous, the pores being in the range of molecular weights of those molecules which are to be replaced. In one embodiment, a liquid formulation comprising the zymogens and fibrinogen is passed through a column that is packed with the porous resin. The zymogens and fibrinogen in the solution will be too large to enter the pores of the resin and will quickly pass through the column. Without being bound by the mechanism, small molecule in the solution or formulation e.g. the reversible inhibitors, will travel a more tortuous path, as they are able to enter and re-exit the pores of the resin, thus greatly slowing their rate of migration through the resin bed. Those small molecule with which the resin has been pre-equilibrated enjoy an advantage of a significant head-start, and therefore exit the resin together with the proteins (the zymogens and fibrinogen). Thus, the buffer salts and other small molecules are exchanged in this step.

In some embodiments, the at least one vitamin K-dependent clotting zymogen inhibitor is diluted at the surface of bleeding or non-bleeding wound or an internal or external organ of a subject. The subject may be a human patient. The small molecule exchange device includes for example, water, saline, $CaCl_2$ or other divalent cations, and/or a phospholipid.

In some embodiments, the step of adding the small molecule activator is carried out by passing the formulation through a small molecule exchange device including the small molecule activator prior to or during application to the surface.

In another embodiment, the small molecule is added manually. In some embodiments, the small molecule activator is selected from a phospholipid and a divalent cation, such as a calcium and iron cation. The small molecule exchange device may contain, for example, a calcium cation containing buffer.

In some embodiments of the method of treatment, therapeutic use and/or method of forming/preparing/manufacturing a sealant, the vitamin K-dependent clotting zymogens in the formulation comprise at least Factor II, Factor X and may further comprise Factor VII and/or Factor IX. The source of the vitamin K-dependent clotting zymogens may be, for example, Prothrombin-Proconvertin-Stuart Factor-Antihemophilic Factor B (PPSB) and/or Prothrombin Complex Concentrate (PCC). In some embodiments, the PPSB includes Factors II, VII, IX and X. The PCC may include Factors II, and X and may optionally further include Factor IX, Factor V and/or Factor VII. In one embodiment, the vitamin K-dependent clotting zymogen source is a PPSB concentrate, concentrated by about 2-50 fold compared to the zymogens concentration in plasma, as normalized to Factor IX and/or Factor II. The PPSB concentrate may be concentrated about 4 to 40 fold, about 5 to 40 fold, about 10 fold or about 20 fold.

In some embodiments of the method of treatment, therapeutic use and/or method of forming/preparing/manufacturing a sealant, the formulation includes a pharmaceutically acceptable carrier. In some embodiments, the formulation is a liquid formulation.

In preferred embodiments of the methods, the liquid formulation remains stable for at least 14 days at an ambient temperature of about 2° C. to 8° C. In some embodiments, the liquid formulation remain stable for at least 30 days, 45 days, 60 days, up to 90 days or more, at an ambient temperature of about 2° C. to 8° C.

In some embodiments, the liquid formulation is stable for about or at least 7 days at an ambient temperature in a range of about 2° C. and up to room temperature.

In certain embodiments the liquid formulation is stable for about 30 days at room temperature.

In some embodiments, the formulation is free of added thrombin and is essentially free of an irreversible thrombin inhibitor such as hirudin. Preferably, the formulation is free of added antithrombin III or substantially free of antithrombin III, an irreversible thrombin inhibitor.

The inhibitor of at least one of the vitamin K-dependent clotting zymogens is selected from heparin (in the absence of added antithrombin III), a calcium chelator, a reversible serine proteases active site inhibitor and a combination of such inhibitors. The vitamin K-dependent clotting zymogens inhibitor may be heparin. The vitamin K-dependent clotting zymogens inhibitor may be a calcium chelator, for example a citrate ion, oxalate, EDTA, EGTA or a combination of such calcium chelators. In some embodiments, the calcium chelator is a citrate ion, for example provided by sodium citrate.

The formulation may include from about 1 mM to about 50 mM sodium citrate, or from about 5 mM to about 25 mM sodium citrate.

In some embodiments, the calcium chelator is EDTA and/or EGTA. The formulation may include from about 0.1 mM to about 2.5 mM EDTA and/or EGTA. In some embodiments, the calcium chelator is oxalate. The formulation may include a combination of a citrate ion and EDTA and/or EGTA, for example sodium citrate and EDTA.

In some embodiments of the method of treatment, therapeutic use and/or method of forming/preparing/manufacturing a sealant, the at least one reversible inhibitor of at least one vitamin K-dependent clotting zymogen in the formulation is a serine protease active site inhibitor, for example arginine, lysine, benzamidine or a combination of such reversible serine protease active site inhibitors. The formulation may include arginine in an amount of from about 0.1% to about 5% (w/v) arginine, from about 0.5% to about 4%, or about 1%, 1.5%, 2%, 2.5%, 3%, 3.5%, or 4% arginine.

In some embodiments of the method of treatment, therapeutic use and/or method of forming/preparing/manufacturing a sealant, the ratio of PP SB, vitamin K-dependent clotting zymogens or PCC (U) to fibrinogen (mg clotable protein) in the formulation is about 0.01 to about 1.0, as normalized to Factor IX and/or Factor II. In some embodiments, the ratio is about 0.05 to about 0.2, or about 0.1 to about 0.2.

Further provided is a container comprising a formulation disclosed herein. In some embodiments, the container is an ampoule, a vial, a test tube or a syringe and the like. The formulation may be liquid or solid.

In various embodiments, provided is a syringe or an applicator containing the formulation of the invention that is attached to a small molecule exchange device. The device comprises a small molecule activator of a vitamin K-dependent clotting zymogen. The small molecule activator may be for example, a phospholipid, or a divalent cation, such as a calcium cation and or iron cation. The small molecule exchange device may contain, for example, a calcium cation containing buffer.

In another aspect, provided is a kit comprising a container such as an ampoule, a vial or syringe which includes the formulation as disclosed hereinabove; optionally the kit includes a small molecule exchange device and/or instructions for use. A kit may include at least one container and at least one label. Suitable containers include, for example, ampoules, vials, syringes and test tubes. The containers can be made of for example, glass, metal or plastic.

In some embodiments, the small molecule exchange device is a gel filtration column, for example a disposable desalting column of about 0.5 to about 5 ml for use by gravity flow and/or centrifugation. The device may include a solvent, for example water or saline, and/or may include a small molecule activator of at least one of the vitamin K-dependent clotting zymogens, such molecule being for example $CaCl_2$. The device may also be any commercially available gel filtration device of any conformation.

Further disclosed herein is a method of manufacturing a sealant formulation according to the invention, the method includes the steps of:

a) providing a fibrinogen component;
b) providing a component comprising the vitamin K-dependent clotting zymogens comprising at least FII, FX and optionally FIX and/or FVII;
c) providing a component comprising at least one reversible inhibitor of at least one of the vitamin K-dependent clotting zymogens; and d) admixing the components of a) to c); wherein the admixed components are free of added irreversible thrombin inhibitor.

The components can be provided in any combination, for example the fibrinogen component can be combined with the component comprising the reversible inhibitor; the fibrinogen component can be combined with the vitamin K-dependent clotting zymogens component; and/or the vitamin K-dependent clotting zymogens component can be combined with the reversible inhibitor.

The term "admixing" means mixing the components in any order, any combination and/or sub-combination.

In some embodiments, at least one of the components comprises FV. In another embodiment, an additional component comprising FV is admixed with components a) to c).

In some embodiments, at least one of the components is provided in liquid form, thereby resulting in a liquid formulation.

A liquid formulation can be dried by including a drying step such as lyophilization.

In one embodiment, the method of manufacture further comprises a drying step, thereby resulting in a dry formulation.

Further provided is a sealant formulation obtainable by the method of manufacturing a sealant formulation according to the invention.

In another aspect, the invention provides a sealant formulation comprising fibrinogen; vitamin K-dependent clotting zymogens comprising at least Factor II, Factor IX and Factor X; and at least one reversible inhibitor of at least one of the vitamin K-dependent clotting zymogen, wherein the formulation is free of added irreversible thrombin inhibitor. In another aspect, the invention provides a method for preparing a sealant at a surface comprising: providing the formulation disclosed hereinabove; and applying the formulation to the surface under conditions which facilitate fibrin polymerization at the surface.

In certain embodiments, the conditions which facilitate fibrin polymerization comprise removing, neutralizing, blocking and/or diluting the reversible inhibitor of at least one of the vitamin K-dependent clotting zymogens by passing the formulation through a small molecule exchange device prior to or during application to the surface of a subject. In some embodiments, the at least one vitamin K-dependent clotting zymogen inhibitor is diluted at the surface of bleeding or non-bleeding wound or an internal or external organ of a subject. The subject may be a human patient. The small molecule exchange device includes for example, water, saline, $CaCl_2$ or other divalent cations and/or a phospholipid.

In various embodiments, the removing, blocking, neutralizing, or diluting the inhibitor of at least one of the vitamin K-dependent clotting zymogens is carried out by applying the formulation directly to a surface of a body part of a subject. For example, the surface may be a blood vessel or bleeding tissue or organ.

In another aspect, the invention provides a calcium-free sealant formulation. Such formulation can be obtained by capturing all calcium initially present in one of the components e.g. capturing the calcium by using a chelator such as EDTA or EGTA, and removing the calcium-chelator complex formed e.g. by using a size exclusion filter.

Accordingly, provided herein is a calcium-free sealant formulation e.g. in liquid form comprising fibrinogen; and vitamin K-dependent clotting zymogens comprising at least Factor II, Factor X, and optionally Factor IX.

The term "calcium-free" means that the formulation contains less than 1.25 mmol/L. In one embodiment, the formulation is also free of added irreversible thrombin inhibitor.

In some embodiments, such calcium-free formulation is free of a chelating agent.

In some embodiments, the vitamin K-dependent clotting zymogens further comprise Factor VII.

In some embodiments, the vitamin K-dependent clotting zymogens are a PPSB, PPSB plasma fraction or PCC.

In some embodiments, the vitamin K-dependent clotting zymogens are a PPSB plasma fraction or PCC.

In some embodiments, the formulation is free of added thrombin.

In some embodiments, the irreversible thrombin inhibitor is selected from the group consisting of hirudin, small molecule thrombin inhibitors, and antithrombin III.

The reversible and irreversible inhibitors mentioned herein can be synthetic or natural.

The vitamin K-dependent clotting zymogens may be a concentrate, concentrated by about 2-50 fold compared to the vitamin K-dependent clotting zymogens concentration in plasma, as normalized to Factor IX and/or Factor II, for example a Prothrombin Complex Concentrate (PCC) of PPSB. In some embodiments, the PCC is a three-factor PCC or a four-factor PCC. The ratio of PPSB or PCC (U) to fibrinogen (mg clottable protein) is about 0.01 to about 1.0 as normalized to Factor IX and/or Factor II.

The formulation may further comprise a reversible inhibitor of at least one of the vitamin K-dependent clotting zymogens wherein the inhibitor of at least one of the vitamin K-dependent clotting zymogens is selected from the group consisting of heparin (in the absence of added antithrombin III), a serine protease active site inhibitor and a combination of such inhibitors of the vitamin K-dependent clotting zymogens.

In some embodiments, the reversible inhibitor of at least one of the vitamin K-dependent clotting zymogens is a serine protease active site inhibitor. In some embodiments, the serine protease active site inhibitor is selected from the group consisting of arginine, lysine, benzamidine and a combination of such serine protease active site inhibitors. In one embodiment, the serine protease active site inhibitor is arginine.

The formulation may be used in hemostasis, sealing, tissue adhesion, graft fixation, wound healing or anastomosis.

Further provided is a method for preparing a sealant at a surface comprising: providing the liquid, calcium-free formulation and applying the formulation to the surface under conditions which facilitate fibrin polymerization at the surface.

In some embodiments, the surface is a blood vessel or an internal or external body organ.

In some embodiments, the conditions comprise adding a small molecule activator of vitamin K-dependent clotting zymogens e.g. calcium cation, thereby causing fibrin polymerization.

In various embodiments, the addition of the small molecule activator is carried out by passing the formulation through a small molecule exchange device prior to or during application to the surface of a subject. The small molecule exchange device includes for example, water, saline, $CaCl_2$ or other divalent cation and/or a phospholipid.

The formulations according to the invention may be kept in a container, for example an ampoule, test tube, a vial or a syringe.

Further provided is a kit comprising the formulation or the container according to the invention, a small molecule exchange device; and optionally instructions for use.

Further provided is a method of manufacturing the calcium-free sealant formulation comprising the steps:
a) providing a fibrinogen component;
b) providing a component comprising vitamin K-dependent clotting zymogens comprising at least FII, FX and optionally FIX and/or FVII;
c) optionally providing the inhibitor of at least one of the vitamin K-dependent clotting zymogens;
d) admixing the components of a) and b) or a) to c).

In one embodiment, each of the components a) to c) is free of an irreversible thrombin inhibitor.

In some embodiments, at least one of the components is provided in liquid form, thereby resulting in a liquid formulation. In some embodiments, the formulation is dried.

In another aspect, provided is a method of providing hemostatic treatment; graft fixation, wound healing and/or anastomosis, to a surface in a subject, comprising applying to the surface a calcium-free sealant formulation comprising an effective amount of fibrinogen; and vitamin K-dependent clotting zymogens comprising at least FII, FX, and optionally an inhibitor of at least one of the vitamin K-dependent clotting zymogens and/or Factor IX and/or Factor VII; wherein the formulation is free of an irreversible thrombin inhibitor.

The sealant formulation can be used for treating, without limitation, abdominoplasty; tissue healing; burn treatment; and dura sealing, hemostasis; graft fixation; wound healing; anastomosis. The surface maybe a bleeding or non-bleeding surface.

The invention provides a method of healing and/or reducing blood loss in a subject in need, comprising applying to the subject a therapeutically effective amount of a formulation according to the invention.

The term "a therapeutically effective amount" refers to the dose required to prevent, ameliorate, and/or treat a disease, disorder or condition. The effective dose can be changed depending on the age and weight of the subject, the disease or condition, its severity and other factors which can be recognized by the skilled in the art.

In another aspect, provided is a calcium-free sealant formulation comprising an effective amount of fibrinogen; and vitamin K-dependent clotting zymogens comprising at least FII, FX, and optionally a reversible inhibitor of at least one of the vitamin K-dependent clotting zymogens and/or FIX; wherein the formulation is free of an irreversible thrombin inhibitor for use in hemostasis; graft fixation; wound healing; anastomosis. The use includes, without limitation, abdominoplasty; tissue healing; burn treatment; and dura sealing, The vitamin K-dependent clotting zymogens in the formulations disclosed herein may further comprise Factor IX and or Factor VII.

The formulations disclosed herein may further comprise Factor V.

The fibrinogen can be prepared from initial blood composition. The blood composition can be whole blood or blood fractions, i.e. a product of whole blood such as plasma. Fibrinogen can be autologous, human including pooled plasma, or of non-human source. It is also possible that the fibrinogen is prepared by recombinant methods or can be chemically modified.

In one embodiment of the invention, the fibrinogen solution is comprised from a biologically active component (BAC) which is a solution of proteins derived from blood plasma which can further comprise anti fibrinolytic agents such as tranexamic acid and/or stabilizers such as arginine, lysine, their pharmaceutically acceptable salts, or mixtures thereof. BAC can be derived from cryoprecipitate, in particular concentrated cryoprecipitate.

The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitate that contains fibrinogen and factor XIII. The precipitate can be collected, for example by centrifugation and dissolved in a suitable buffer such as a buffer containing 120 mM sodium chloride, 10 mM trisodium citrate, 120 mM glycine, 95 mM arginine hydrochloride. The solution of BAC can comprise additional factors such as for example factor VIII, fibronectin, von Willebrand factor (vWF), vitronectin, etc. for example as described in U.S. Pat. No. 6,121,232 and WO9833533. The composition of BAC can comprise stabilizers such as tranexamic acid and arginine hydrochloride. The amount of tranexamic acid in the solution of BAC can be from about 80 to about 110 mg/ml.

In another embodiment, the concentration of plasminogen and plasmin in the BAC composition is lowered to equal or less than 15 μg/ml like for example 5 μg/ml or less plasminogen e.g. using a method as described in U.S. Pat. No. 7,125,569, EP 1,390,485 and WO02095019. In another embodiment of the invention, when the concentration of plasminogen and plasmin in the BAC composition is lowered, the composition does not contain tranexamic acid or aprotinin.

The fibrinogen solution may be the BAC2 component (from EVICEL®) or any other fibrinogen containing solution, such as purified recombinant fibrinogen or cryoprecipitate produced from human plasma.

These and other aspects and embodiments of the invention will become evident upon reference to the following detailed description of the invention and the figures.

DETAILED DESCRIPTION OF THE INVENTION

Figure 1:
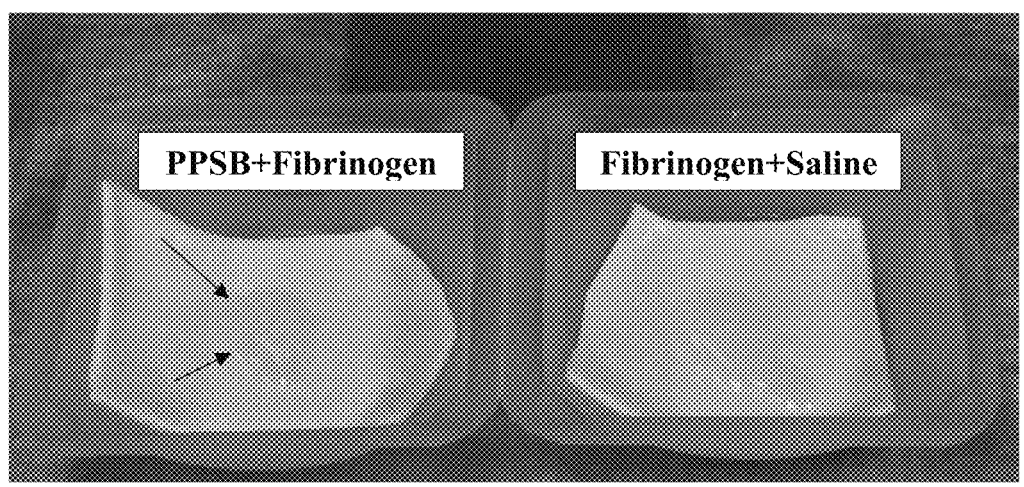
FIG. 1 shows fibrin clotting of a PPSB/BAC2 (BAC2 as a source of fibrinogen) liquid formulation after its application onto a piece of corium (derived from bovine hide) coated with tissue factor and calcium. Clot formation was determined by monitoring the gelation of the formulation, and the fact that the formulation ceased to flow. Formation of thrombin (left dish, arrows) was observed by coloration (a chromogenic substrate for thrombin was added to the samples) of the clot 30 seconds after application to the coated-corium. The FIG. shows the clot 3 minutes after the application. No clotting or color was observed with a liquid solution comprising saline and BAC2 (right dish).

In one aspect the invention relates to a sealant formulation comprising fibrinogen; vitamin K-dependent clotting zymogens comprising at least Factor II and Factor X; and a reversible inhibitor of at least one of the vitamin K-dependent clotting zymogens, wherein the formulation is free of an added irreversible thrombin inhibitor.

The present invention is based, in part, upon the finding that a single formulation comprising prothrombin zymogens (e.g. PPSB including Factors II, IX, X, and VII) and fibrinogen (e.g. BAC2) is useful as a biological sealant, is stable and exhibits a long shelf life, as determined by the capability of the formulation to form a clot e.g. after a prolonged storage. Stability can be determined by observing minimal or absence of spontaneous clotting in the formulation e.g. the formulation does not show or have spontaneous clotting in the absence of an activator, such as free calcium, and has an acceptable clotting activity level upon exposure to the activator.

It was found that storing a PPSB:fibrinogen formulation at 2-8° C. for up to 28 days or up to 90 days resulted in a stable formulation having a fast clotting time upon $CaCl_2$ addition. Without wishing to be bound to theory, following storage at 2-8° C. a conversion of Factor X, VII and/or IX zymogens to an active conformation may occur albeit the inhibition of arginine and citrate, thereby shortening the required time for generation of active thrombin (after addition of calcium) and consequently of clot formation. It was found that this fast clotting is prevented when the 2-8° C. stored formulation comprised 0.125 IU/mL heparin.

It was found that storing a PPSB:fibrinogen formulation at RT for up to 28 days resulted in a stable formulation having a substantially unaltered clotting time upon $CaCl_2$ addition.

In one embodiment, the formulation comprises Factor X, VII and/or IX in their active form.

It was found that fast clotting time was obtained in the presence of both, $CaCl_2$ and tissue factor.

In another aspect, the invention relates to a formulation free of calcium and includes fibrinogen and vitamin K-dependent clotting zymogens comprising at least Factor II and Factor X.

In some embodiments, the formulations further comprise factor IX and/or Factor VII.

The present invention is based, in part, upon the finding that a single formulation comprising prothrombin zymogens and fibrinogen is useful as a biological sealant, is stable and exhibits a long shelf life, as determined by the capability of the formulation to form a clot. Stability can be determined by observing minimal or absence of spontaneous clotting in the formulation e.g. the formulation does not show or have spontaneous clotting in the absence of an activator, such as free calcium, and has an acceptable clotting activity level upon exposure to the activator.

The terms "stable", and "stability" when referring to a liquid mixture, mean substantially an absence of fibrin polymerization/clotting in the formulation before it contacts the activator and/or before the reversible inhibitor is removed, neutralized, blocked, and/or diluted.

The clotting activity level or capability of the formulation to form a sealant can be determined in-vitro and/or in-vivo. Stability can also be determined by measuring and/or observing the presence of minimal or absence of fibrin formation in the shelf-ready aqueous formulation.

Clotting can be measured, for example, by measuring migration length on a slanted surface (or drop test model) or by any other method known in the art. Full clotting can be assessed by cessation of flow of the liquid formulation e.g. upon inversion. Rapid polymerization can be measured using a Stat4 clotting analyzer Stago Diagnostics or equivalent coagulometer.

An acceptable clotting activity level means, for example, the ability of the formulation to form a clot within 30 minutes or less following calcium addition, and under 5 minutes following calcium and tissue factor addition; and/or in-vivo, for example, within under 5 minutes following calcium addition and/or contact with tissue factor (for example, endogenous tissue factor).

In one embodiment the ability of the formulation to form a clot ranges between 30 seconds and 120 seconds on a bleeding surface containing tissue factor, and between 60 seconds and 600 seconds on a non-bleeding surface.

Prothrombin, the inactive precursor of thrombin, does not display proteolytic activity until the active form of the enzyme is generated by proteolytic cleavage of prothrombin by Factor Xa (activated Factor X). When desired, prothrombin can be activated to thrombin to convert fibrinogen to fibrin and attendant fibrin polymerization. Prothrombin and fibrinogen, in contrast to thrombin and fibrinogen, are stable together in solution.

In one embodiment in the formulation disclosed herein, prothrombin (Factor II) is included together with Factor X for its activation. Factor VII and factor IX are optionally included. Without wishing to be bound to theory, the presence of prothrombin, and the attendant absence of thrombin, provides a formulation in which the kinetic conversion of fibrinogen to fibrin may be well-controlled. The fibrin sealant may, therefore, be used in indications where the classic sealant is ineffective, for example graft fixation. Endogenous activated zymogens may facilitate conversion of prothrombin to thrombin at the wound site.

In one embodiment, a mixture of inactive enzyme precursors (also called zymogens) is referred to as PPSB.

In some embodiments, a concentrate of the PPSB is a prothrombin complex concentrate (PCC). The PCC can be a three-factor PCC (3F-PCC) with FII, FIX and FX, or a four-factor PCC (4F-PCC) which also includes Factor VII.

Disclosed herein is a fibrin sealant in which all the components required to form a fibrin are found in a single formulation which can be applied from a single syringe, which improves ease of use and convenience.

As used herein, the indefinite articles "a" and "an" mean "at least one" or "one or more" unless the context clearly dictates otherwise.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate +/−10%.

"Thrombin" or "thrombin polypeptide" is a mammalian serine protease which is part of the blood coagulation cascade and converts fibrinogen into fibrin monomers which assembly into insoluble strands of fibrin, as well as catalyzing other coagulation-related reactions. In humans, prothrombin is encoded by the F2 gene, and the resulting polypeptide is proteolytically cleaved in the coagulation cascade to form thrombin. Thrombin serves, inter alia, as an active component in several hemostasis products. For example, fibrin sealants typically comprise a fibrinogen component and a thrombin component. When both components are mixed (e.g. when applied to a bleeding wound) thrombin cleaves fibrinogen and a fibrin polymer is formed.

Thrombin is a serine protease which results from the cleavage of prothrombin (Factor II), a zymogen precursor, by another serine protease (Factor Xa). Human thrombin is a 295 amino acid protein composed of two polypeptide chains joined by a disulfide bond.

Various thrombin inhibitors are recognized in the art. An irreversible thrombin inhibitor comprises a group of molecules that covalently bind thrombin or bind thrombin with a very high affinity and/or a group of molecules that destroy a functional group on thrombin or render the thrombin inactive. For example, hirudin and antithrombin III are considered herein as such irreversible thrombin inhibitors. Thrombin binds to antithrombin III such that thrombin is not released from the complex. As used herein, a thrombin inhibitor that binds thrombin with a high affinity (sub-microM) is considered irreversible. One such example is hirudin, which binds thrombin in the picoM range.

In some embodiments, the formulation disclosed herein is free of added thrombin, and is free of a thrombin inhibitor. The vitamin K-dependent clotting zymogens may be provided as, for example, PPSB or PCC. An example of a 20× fold PCC concentrate is Octaplex® (Octapharma, Vienna). Non-limiting examples of PCC include Beriplex®, Ocplex®, Kcentra®, Cofact®, among others.

For long-term storage, the formulation is aliquoted into sterile vials, ampoules, or other containers, for example a syringe or other applicator, which are then sealed. In one embodiment, a container that permits removal of the formulation with a syringe through the seal is used. The container is labeled according to standard practice in the pharmaceutical or medical device field. For use, the sealant formulation can be used directly from the container according to the needs of the individual patient and on the severity of bleeding. The formulation can be applied to bleeding tissue to achieve hemostasis.

The liquid formulation disclosed herein is advantageous in that it remains stable for at least 14 days, 30 days, 45 days, 60 days or up to 90 days, at an ambient temperature of about 2° C. to 8° C. or at least 7 days at an ambient temperature in a range of about 2° C. and up to room temperature or for about 30 days at room temperature.

The formulation is assessed for stability by testing its capability to form a sealant when (i) removing, diluting, neutralizing and/or blocking the inhibitor of at least one of the vitamin K-dependent clotting zymogens and/or (ii) adding a small molecule activator of the vitamin K-dependent clotting zymogens.

The formulation according to the present invention can be frozen or lyophilized.

Inter alia, the advantages of the present formulations are manifold and can be at least one of the following: long shelf life, for example, stable as defined herein; good control of the kinetics of fibrin generation, for example, effectively no premature polymerization; purification of thrombin is not required, thereby reducing the cost associated with manufacturing; and/or easy to use and convenient to prepare; i.e. fewer components and no assembly required by attending practitioner.

The term a "pharmaceutically acceptable carrier" refers to any diluent or a vehicle which is suitable for human or other animal use. E.g. "a pharmaceutically acceptable carrier or diluent" refers to reagents, compounds, materials, compositions, diluents that are compatible with the constituents in the formulation and suitable for use in contact with the tissues of human beings and animals without excessive toxicity, irritation, allergic response, or other complication commensurate with a reasonable benefit/risk ratio. A pharmaceutically acceptable carrier suitable for use with the formulation disclosed herein includes liquids, semi-solid and solid materials.

A "surface" is a position or location where one desires to form the sealant or glue. The surface depends on the use of the sealant. The sealant may be used, for example, in hemostasis, tissue fixation, graft fixation, wound healing and anastomosis. The formulations, methods, and kits disclosed herein can be used internally and externally, for tissue and organ graft fixation, for sealing a surgical wound, in vascular surgery including providing hemostasis and for anastomoses such as arterial, gastrointestinal and tracheal anastomoses.

The surface can be an external surface of the skin that can be seen by unaided vision and a surface of an internal body part which is a part of the internal anatomy of an organism. External surfaces include, but are not limited to, the skin of the face, throat, scalp, chest, back, ears, neck, hand, elbow, hip, knee, and other skin sites. Examples of internal body parts include, but are not limited to, body cavity or anatomical opening that are exposed to the external environment and internal organs such as the nostrils; the lips; the ears; the genital area, including the uterus, vagina and ovaries; the lungs; the anus; the spleen; the liver; and the cardiac muscle. The surface can be a bleeding or a non-bleeding site. The surface can also be a working surface outside the body.

A "subject" as used herein, includes animals of mammalian origin, including humans. In one embodiment, a subject is a surgery patient or a wounded patient.

While the following examples demonstrate certain embodiments of the invention, they are not to be interpreted as limiting the scope of the invention, but rather as contributing to a complete description of the invention.

EXAMPLES

Example 1

Preparation of a Single Component Sealant Formulation Comprising Vitamin K-dependent Clotting Zymogens and Fibrinogen PPSB, a source of the vitamin K-dependent clotting zymogens, was standardly produced as described in the art (Production of plasma proteins for therapeutic use. Joseph Bertolini, Neil Goss, John Curling. 2013 Wiley Press).

Briefly, concentrated PPSB, was produced by loading cryo-depleted human plasma on a DEAE anion exchange column and eluting with a concentrated salt solution (0.25M NaCl) which also includes 10 mM sodium citrate (NaCitrate). The PPSB was concentrated between 4-16 fold vs. plasma as determined by the prothrombin concentration (Factor II).

The mixture comprised all of the vitamin K-dependent clotting zymogens that typically bind to anion exchange columns (such as FVII, FIX, protein C and protein S, and FX), their associated co-zymogens (FV and FVIII) and any other proteins that are co-eluted.

The vitamin K-dependent clotting zymogens inhibitors (e.g. NaCitrate, EDTA) served to chelate calcium ions and prevent premature activation of any of the prothrombin complex comprising FII, FV, and FX, or any other $Ca^{2+}$ dependent process such as the Tenase complex activation (FVIII and FIX) or FXIII activation.

A 10-fold PPSB concentrate was added to a fibrinogen solution, the mixture comprised between 3-4% concentration of clottable protein (7% fibrinogen diluted 1:1 with PPSB). The fibrinogen solution used in the Examples was BAC2 (a fibrinogen comprising component from EVICEL® Fibrin Sealant). Final ratio between FIX and fibrinogen was 0.14 units/mg (i.e. 0.14 Units (U) FIX per mg fibrinogen). This mixture was shown to be stable at 2°-8° C. for at least three months without showing any premature fibrin clot formation.

Example 2

Clot Formation Using the Single Component Sealant Formulation

To assess the ability of the single component sealant formulation to form a clot, a simulated bleeding site was created by using a piece of corium (bovine hide) coated with a layer of PT (Prothrombin Time) reagent containing tissue factor (Diagnostica Stago STA Neoplastin CI Plus, Cat #00606) and calcium, at about 15-25 mM.

A liquid solution comprising equal volumes of PPSB and BAC2 (as prepared in Example 1) was applied to the tissue factor coated corium and the rate of clot formation was assessed by, the PT assay, a test that measures how long it takes to form a clot, typically, after addition of tissue factor and calcium.

The arginine present in BAC2 has an inhibitory effect on thrombin activity, however, it is not sufficient to completely inhibit or inactivate the thrombin which is generated (from prothrombin) via the tissue factor pathway. Typically, NaCitrate, present in the BAC2 and PPSB, inhibits generation of active enzymes by chelating calcium. However, the PT reagent contains calcium at a level sufficient to overcome the NaCitrate inhibitory effect.

Clotting was initially observed ~30 seconds after applying the liquid solution onto the coated corium and the clot was fully solid after about 1 minute and 30 seconds. As a control, a solution comprising equal volumes of BAC2 and saline was applied to the coated-corium and assessed for clot formation. In the absence of PPSB, no clot was formed during the observation period (more than 30 minutes).

To further evaluate the enzymatic properties of the liquid sealant formulation (PPSB/BAC2), a chromogenic thrombin substrate [H-D-Phenylalanyl-L-pipecolyl-L-arginine-p-nitroaniline dihydrochloride. S-2238TM Chromogenix] was added to the two samples (PPSB/BAC2 and BAC2/saline). The PPSB/BAC2 sample (left dish in FIG. 1) turned yellow due to thrombin generation and cleavage of the chromogenic substrate. However, the BAC2/saline sample (right dish) did not turn yellow, indicating that thrombin was not generated in the sample.

FIG. 1 shows coloration of the PPSB/BAC2 clot after incubation of three minutes (left). This coloration was already evident 30 seconds after the application. No color was observed with the BAC2/saline sample (right).

Example 3

Effect of Zymogens (PPSB) to Fibrinogen Ratio on Clotting Time

In this experiment, BAC2 having a fibrinogen concentration of 70 mg/mL and PPSB, both as described above were used. The amount of Factor IX and prothrombin (Factor II) present in the PPSB was approximately 10-fold more than the amount present in plasma, i.e. about 9.8 IU/ml Factor IX and 10 IU/mL Factor II. PPSB and BAC2 were mixed in different ratios, see FIG. 2A, and the clotting time was measured by the PT assay using a coagulation analyzer (Diagnostica Stago Start4). Clotting was induced by adding the Neoplastin PT reagent which comprises, both calcium and tissue factor which bind to Factor VII thereby initiating the extrinsic pathway of coagulation. 100 µL Neoplastin PT reagent (kept well mixed at 37° C.) was combined with 500 µL of test sample (the BAC2 and PPSB mix at the different volume ratios e.g. 90:10, 80:20, 70:30 and so on, respectively). The test sample was incubated at 37° C. for 60 seconds prior the assay in the incubation wells of the analyzer. The concentration of fibrinogen was variable depending on the volume ratio of BAC2 and PPSB, however, in any case the fibrinogen was present in the sample in excess (even if diluted 20:1 with PP SB), and therefore, without being bound to theory, the rate limiting factor was the rate of enzyme activation.

Figure 2A:
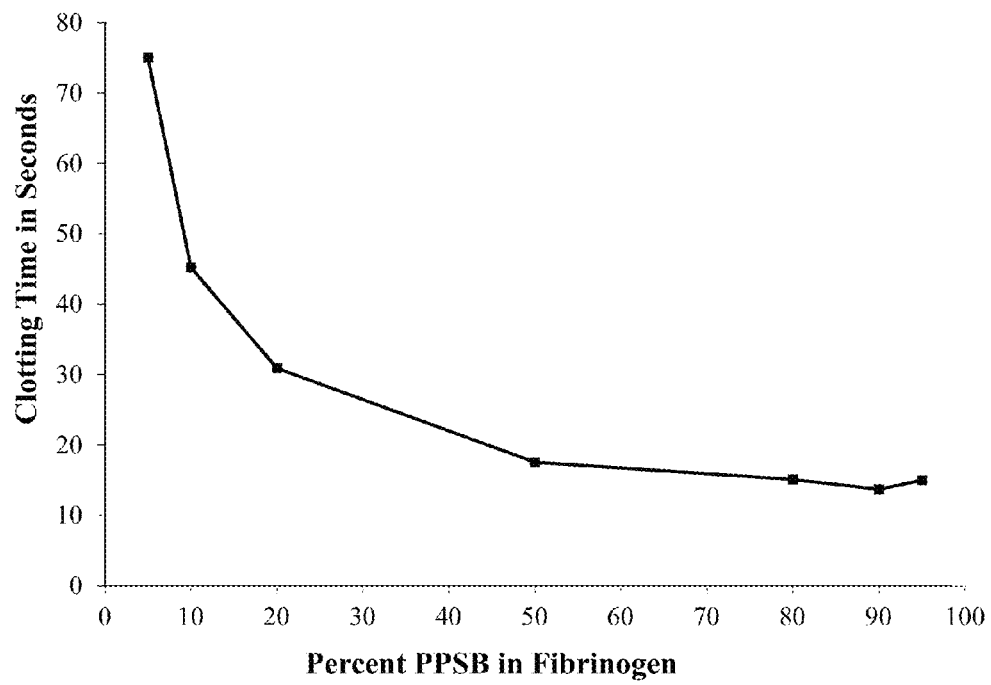
FIG. 2A is a graph showing the effect of adding an increasing percentage of PPSB prepared at 10× concentration (10 IU Factor II/ml) to BAC2 (fibrinogen) on clotting time.
Figure 2B:
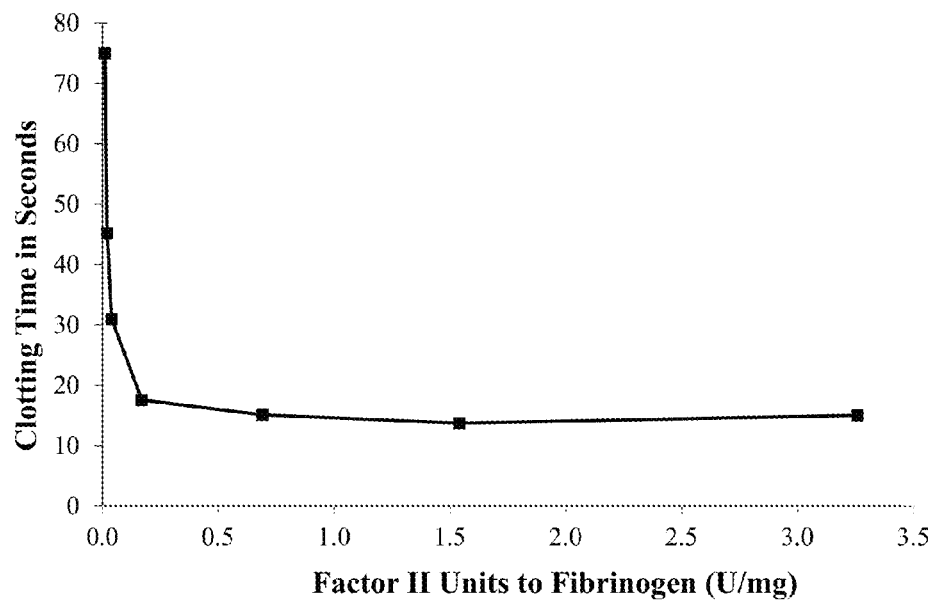
FIG. 2B is a graph showing the effect of changing the ratio of Factor II and BAC2 on clotting time.

FIGS. 2A.-2B and Table 1 show the clotting time of the different formulations. FIG. 2A shows clotting as a function of PPSB percent in BAC2, and FIG. 2B and Table 1 shows clotting as a function of the ratio of Factor II to fibrinogen (U per mg). Typically, Factor II is used to express the activity of PPSB in commercially available products. The amount of Factor IX and prothrombin present in the PPSB is approximately 10 fold more than the amount present in plasma, i.e. 10 IU/mL Factor II.

TABLE 1

Clotting time (in sec) of PPSB:BAC2 solution having different FII to Fibrinogen ratios (Units per mg).

| Clotting Time sec | FII to Fibrinogen U/mg |
|---|---|
| 15.0 | 3.26 |
| 13.7 | 1.54 |
| 15.1 | 0.69 |
| 17.6 | 0.17 |
| 30.9 | 0.04 |
| 45.2 | 0.02 |
| 75.0 | 0.01 |

The results in FIG. 2A and Table 1 show that increasing PPSB volume (as normalized by Factor II) compared to the fibrinogen (BAC2) volume decreased the clotting time of the mixture. At 50% PPSB in BAC the clotting time was about 17.5 sec, and decreased slightly with higher amounts of PPSB.

Example 4

Effect of Substituting Plasma for PPSB

The present experiment examines the effect of using plasma instead of PPSB in the formulation.

Formulations comprising plasma/BAC2 and PPSB/BAC2 were prepared at the following volume ratios: 1-50% PPSB+50% BAC2; 2-20% PPSB+80% BAC2; 3-20% plasma+80% BAC2; and 4-50% plasma+50% BAC2. PPSB was prepared as in Example 1 (10× concentrated FIX, FII compared to plasma), As in Example 3 above, clotting was induced with tissue factor (TF) and calcium.

Figure 3:
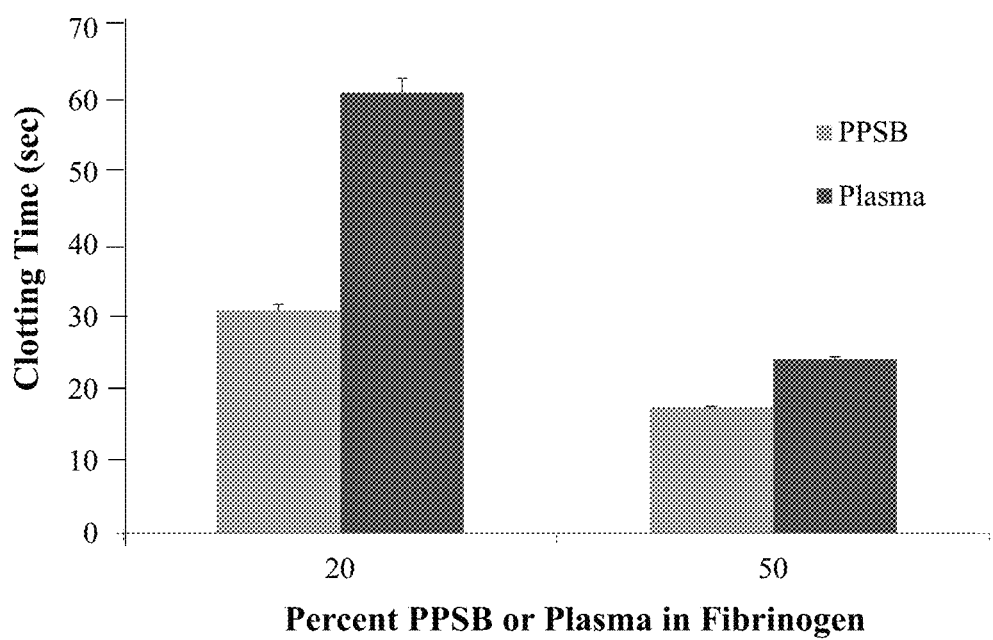
FIG. 3 shows clotting time of a formulation which includes PPSB prepared at 10× concentration (10 IU Factor II/ml) and BAC2 versus a formulation which includes plasma and BAC2 in different ratios.

The results in FIG. 3 show that using equal volume percentage formulations (1-4 and 2-3), a faster clotting time was obtained with the PPSB/BAC2 formulation (1 and 2) as compared to the plasma/BAC2 formulation (3 and 4, respectively).

These results demonstrate that PPSB, which is enriched in vitamin K-dependent clotting zymogens, and fibrinogen can be used to accelerate clot formation.

Example 5

Fibrin Clot Formation Using a Small Molecule Exchange Column

A formulation comprising PPSB and BAC2 was prepared as follows: PPSB was prepared as in Example 1 and mixed at a one to one volumetric ratio with BAC2, finally yielding approximately 3.5% (w/v) clottable protein [the initial BAC2 contains 70 mg/ml (or 7% clottable protein, mostly fibrinogen)] and a PPSB that was concentrated approximately 5-fold as compared to plasma (approximately 0.14 international units (IU) of Factor II per mg of fibrinogen). The formulation also included 1-2 mM of EDTA, 10 mM NaCitrate, 1% (w/v) arginine*HCl, and glycine and acetate buffer (pH 7.0; the buffer comprised 1% (w/v) glycine and 20 mM acetate).

The formulation was passed through a commercially available buffer exchange spin column (Disposable PD-10 Desalting Columns, Product code: 17-0851-01, GE Healthcare) either pre-equilibrated with $CaCl_2$ solution (40-50 mM) or with water, 1% (w/v) glycine buffer containing 2% (w/v) arginine (but no $CaCl_2$) and flow through formulation was collected in a tube.

Clotting was assessed by inverting the tube containing the buffer-exchanged formulation.

Figure 4A:
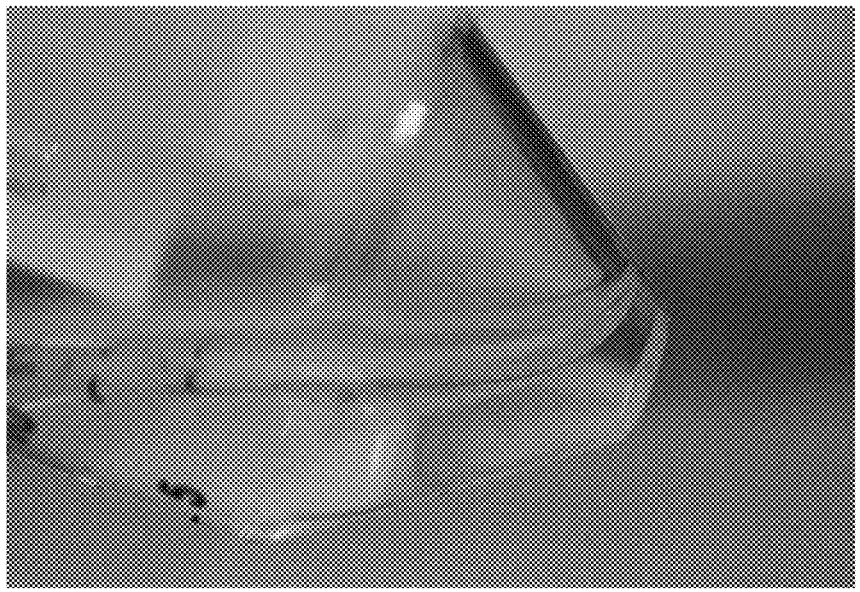
FIG. 4A shows a PPSB-fibrinogen liquid formulation subjected to small molecule exchange by passing the formulation through a commercial column pre-equilibrated with a buffer lacking $CaCl_2$. No clotting occurred even after several days.
Figure 4B:
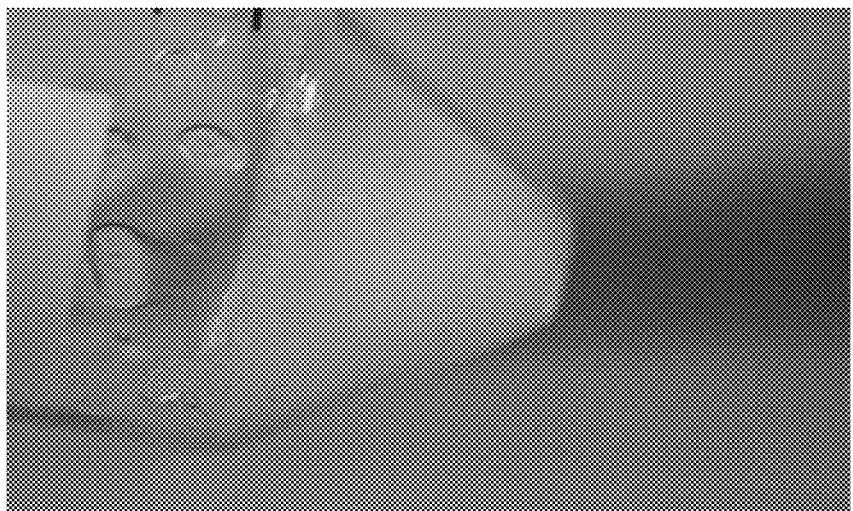
FIG. 4B shows a PPSB-fibrinogen liquid formulation subjected to a small molecule exchange by passing the formulation through a commercial column pre-equilibrated with a buffer including 40 mM $CaCl_2$. Following the exchange, a fibrin clot was spontaneously formed within 12-24 minutes.

The results show that a formulation which passed through the column pre-equilibrated with CaCl2 clotted spontaneously (FIG. 4B) within less than 30 minutes, whereas the formulation which passed through the buffer lacking CaCl2 did not clot, even after several days (FIG. 4A).

Example 6

The Effect of $CaCl_2$ Concentration on the Rate of Fibrin Clot Formation

The following example explores the effect of adding different $CaCl_2$ concentration to the single component sealant formulation on the rate of clot formation.

A 10-fold enriched PPSB10 IU FII/ml):BAC2 formulation (1:1 prepared as in example 1, and without EDTA) was mixed with a PT reagent (a mixture of tissue factor and phospholipids and lacking calcium). $CaCl_2$ at increasing concentrations was supplemented to the mix and the clotting time was measured.

Figure 5:
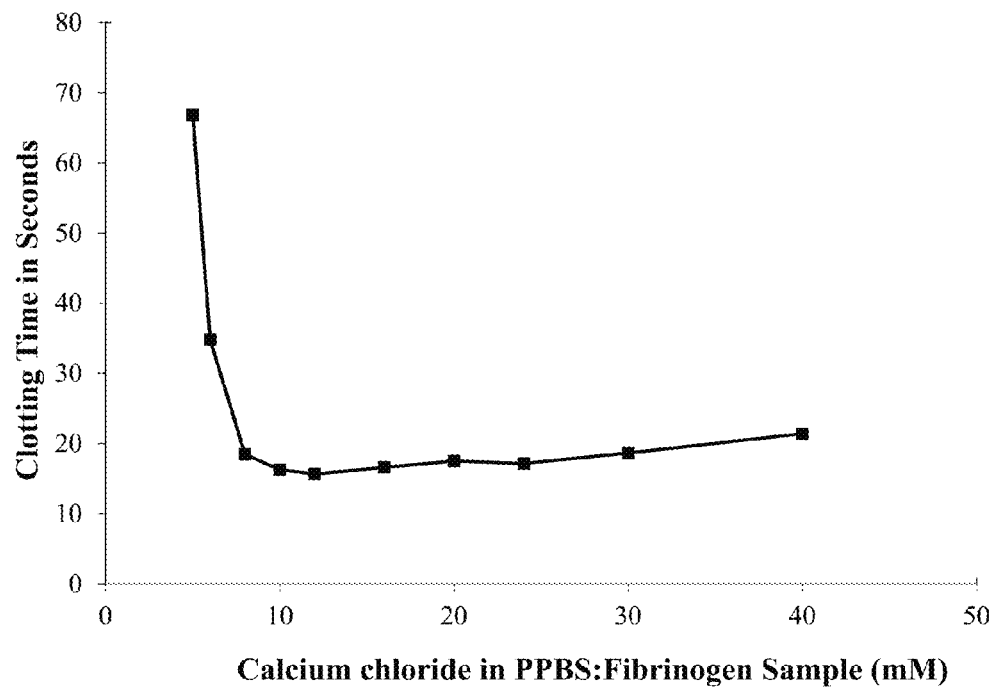
FIG. 5 shows the effect of increasing calcium concentration in a PPSB-BAC2 formulation on clot formation rate (8-40 mM).

Results are seen in FIG. 5. Rapid clotting (<20 seconds as measured using a Stat4 clotting analyzer Stago Diagnostics) was observed at about 8 mM to about 30 mM calcium.

Example 7

Effect of CaCl$_2$ on Clot Formation

It has been found that a clot was formed upon addition of calcium to the stable formulation. In this experiment, PT reagent was not added (i.e. no tissue factor or phospholipids were added). Experiments with 10-fold enriched PPSB (as compared to plasma) mixed 1:1 with BAC2 showed that clotting time could be achieved between 5-10 minutes by adding 10 mM calcium in the absence of tissue factor.

Example 8

Assessment of Stability of PPSB:BAC2 Formulation at 2-8° C.

In this example, the stability of the single component fibrin sealant formulation containing PPSB and fibrinogen was evaluated at a temperature of 2-8° C.

For this purpose, a PPSB-BAC2 formulation (ratio of 0.14 U FII per mg fibrinogen) was incubated at 2-8° C. for different time points (up to 90 days), and the formulation was tested for its ability to form a clot within 30 minutes.

Clot formation was initiated by subjecting the formulation to a PD-10 pre-packed column (Sephadex™ G-25, GE Healthcare 17-0851-01). The column was equilibrated with 5 ml buffer containing 50 mM CaCl$_2$ (Sigma) and 20 mM NaAcetate pH 7.00 (Sigma) three times in gravity mode. An additional 5 ml of CaCl$_2$ were applied to the column and the column was centrifuged for 2 min at 1000 g at 20° C. The column was used to completely remove small molecule inhibitors including EDTA which was present in the formulation at a concentration of 2.5 mM.

The pre-incubated PPSB-BAC2 formulation was warmed for 10 minutes in a 37° C. water bath, applied to the column, the column was centrifuged for 2 min at 1000 g at 20° C. (see Table 2 for the formulation volume applied to the column) and the column flow through solution was collected.

Following collection, time to clot initiation/gelation was assessed in the collected material by visually observing a change in the coloration (from clear to opaque). Also, time to complete clotting was assessed by cessation of flow of the collected material upon inversion.

Results of clot initiation and complete clotting time are presented in Table 2, below.

TABLE 2

Clot initiation and complete clotting time of formulation incubated at 2-8° C. for different periods of time.

| Time point (days) | Volume of mix applied (ml) | Time to clot initiation/ gelation (min) | Time to complete clotting (min) |
|---|---|---|---|
| 0 | 2.5 | 22 | 25 |
| 3 | 2.48 | 19 | 23.5 |
| 7 | 2.45 | 15 | 21 |
| 14 | 2.5 | 14.5 | 19 |
| 30 | 2.5 | 13 | 16.5 |
| 60 | 2.45 | 7.5 | 17 |
| 90 | 2.4 | 6 | 11.5 |

The time to complete clotting was at all times less than or equal to 25 minutes. Some shortening of the required time occurs, without wishing to be bound to theory, by the slow conversion of a small amount of the PPSB zymogens to an active conformation, albeit inhibited by arginine and citrate, thus shortening the required time for the generation of active thrombin. The results indicate that the formulation is stable for at least up to 90 days at a temperature of 2-8° C.

Example 9

Animal Model for In-Vivo Assessment of the Formulation

The rat kidney hemostasis model is a common model to test the ability of a tested formulation to achieve hemostasis (Raccuia J S et al., Am J Surg. 1992. 163(2):234-8. Comparative efficacy of topical hemostatic agents in a rat kidney model).

Briefly, the kidney was dissected out of the side of the peritoneum and pads were placed around it to soak up any bleeding. A clamp was placed on the blood vessels supplying the kidney and a traverse cut was made through the kidney. The tested formulation was applied and the clamp was removed. Bleeding was assessed over a one hour period, after which the total amount of bleeding was weighed. Subsequently, the formulation was scraped off and the bleeding allowed to resume and quantified as low, medium, or high (to assess that the bleeding potential was still existing). All rats were infused with 300 IU heparin/kg animal weight to make the bleeding model more challenging.

One albino rat weighing 406 grams (g) was anaesthetized and subjected to the rat kidney hemostasis model using the PPSB:BAC2 formulation with a final concentration of 5 IU/ml PPSB: 3.5% fibrinogen. A classic 2-component commercial fibrin sealant was used as reference.

Results:

A PPSB:BAC2 formulation was mixed with CaCl$_2$ (25 mM final concentration in the formulation; CaCl$_2$ was manually added into the formulation) and incubated for 15 minutes at room temperature before application to the kidney surface. A clot was formed on the surface immediately upon application and bleeding was completely stopped after 38 minutes. The total blood loss was 5.9 g over the one hour period of the model.

Using a classic 2-component commercial fibrin sealant resulted in immediate clot formation and a total blood loss in the range of 0-10.3 g (in 15 animals). The commercial fibrin sealant was applied directly onto the kidney surface without incubation.

Thus, the all in one PPSB-based fibrin sealant formulation disclosed herein has a good hemostatic potential.

Example 10

Assessment of Stability of PPSB:BAC2 Formulation at RT and 2-8° C. With or without Heparin In this example, the stability of a single component fibrin sealant formulation containing PPSB and fibrinogen was evaluated.

The PPSB was prepared as described in Example 1. BAC2 (Biologically Active Component 2) was used as the fibrinogen component, which contained approximately 100 mg/mL total protein including 70 mg/mL clottable fibrinogen, 20 mg/mL arginine, 10 mM sodium citrate, and excipients including glycine and sodium chloride). The PPSB was combined with BAC2 in equal volumes to generate the single component fibrin sealant formulation.

The samples from the single component fibrin sealant formulation were aliquoted and stored either at room temperature (20-25° C.) or in the refrigerator (2-8° C.).

To a second set of samples, unfractionated heparin at 0.25 IU/mL was added to the PPSB, resulting in a final heparin concentration of 0.125 IU/mL in the single component fibrin sealant formulation.

Figure 6:
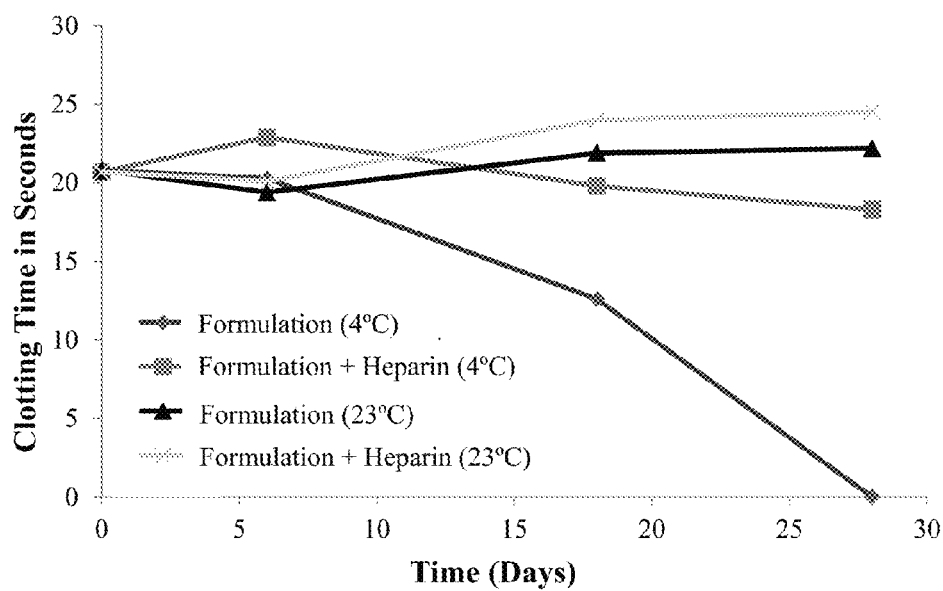
FIG. 6 shows the clotting time for PPSB:fibrinogen liquid formulations with or without heparin stored at 4° C. or 23° C.

Stability was assessed using a standard prothrombin time (PT) assay at various time points over a 28 day period. To perform the PT assay, 50 μL of the sample warmed to 37° C. was combined with 100 μL of PT reagent (Diagnostica Stago STA Neoplastin CI Plus), which consisted of tissue factor and 10 mM calcium. A Diagnostica Stago STart4 coagulation analyzer was used to determine the rate of clot formation. The results are shown in FIG. 6. The results show that at 6 days, clotting times for all of the formulations stored at either temperature with/without heparin were comparable to the baseline clotting time values. The refrigerated formulation without heparin showed a reduction in clotting times at 18 days, and at 28 days the sample was gelled due to activation of clotting factors. No trends in clotting times were observed during the 28 day stability study for the formulation with added heparin stored in the refrigerator or the formulations stored at room temperature.

Although various embodiments have been described herein, many modifications and variations to those embodiments may be implemented. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Citation or identification of any reference in this application shall not be construed as an admission that such reference is available as prior art to the invention.

Section headings are used herein to ease understanding of the specification and should not be construed as necessarily limiting.

The invention claimed is:

1. A storage stable liquid sealant formulation comprising about 1-100 mg/ml fibrinogen; vitamin K-dependent clotting zymogens comprising at least Factor II and Factor X and having a ratio of about 0.01-1.0 IU/mg relative to fibrinogen; and at least one reversible inhibitor of at least one of the vitamin K-dependent clotting zymogens, wherein the sealant formulation is free of an added irreversible thrombin inhibitor; wherein the added reversible inhibitor is selected from the group consisting of 0.125 IU/ml heparin, a about 1-50 mM calcium chelator, about 0.1-5% serine protease active site inhibitor and a combination thereof.

2. The formulation of claim 1, wherein the formulation comprises a pharmaceutically acceptable carrier.

3. The formulation of claim 2, wherein the liquid formulation remains stable at least 7 days at an ambient temperature of about 2° C. and up to room temperature.

4. The formulation of claim 3, wherein the liquid formulation is stable for about 30 days at room temperature.

5. The formulation of claim 1, wherein the formulation further comprises Factor V.

6. The formulation of claim 1, wherein the vitamin K-dependent clotting zymogens further comprise Factor VII.

7. The formulation of claim 6, wherein the vitamin K-dependent clotting zymogens further comprise Factor IX.

8. The formulation of claim 7, wherein Factor X, Factor VII, and/or Factor IX are, at least partially, in their active form.

9. The formulation of claim 1, wherein the formulation is in liquid form and is stable for at least 14 days at an ambient temperature of about 2° C. to 8° C.

10. The formulation of claim 1, being free of added thrombin.

11. The formulation of claim 1, wherein the irreversible thrombin inhibitor is hirudin.

12. The formulation of claim 1, wherein the irreversible thrombin inhibitor is anti-thrombin III.

13. The formulation of claim 1, wherein the vitamin K-dependent clotting zymogens is provided as a concentrate, concentrated by about 2- to 50-fold compared to their concentration in plasma, as normalized to Factor II.

14. The formulation of claim 13, wherein the vitamin K-dependent clotting zymogen concentrate is Prothrombin Complex Concentrate (PCC).

15. The formulation of claim 1, wherein the ratio of the vitamin K-dependent clotting zymogens to fibrinogen is about 0.01 U/mg clottable protein to about 1.0 U/mg clottable protein, as normalized to Factor II.

16. The formulation of claim 1, wherein the reversible inhibitor is a calcium chelator.

17. The formulation of claim 16, wherein the calcium chelator is selected from the group consisting of a citrate ion, oxalate, EDTA, EGTA and a combination of such calcium chelators.

18. The formulation of claim 17, wherein the calcium chelator is a citrate ion.

19. The formulation of claim 18, wherein the citrate ion is provided by sodium citrate.

20. The formulation of claim 19, comprising from about 1 mM to about 50 mM sodium citrate.

21. The formulation of claim 20, comprising from about 5 mM to about 25 mM sodium citrate.

22. The formulation of claim 17, comprising from about 0.1 mM to about 2.5 mM EDTA and/or EGTA.

23. The formulation of claim 1, wherein the reversible inhibitor is a serine protease active site inhibitor.

24. The formulation of claim 23, wherein the reversible inhibitor is arginine.

25. The formulation of claim 24, comprising from about 0.1% to about 5% (w/v) arginine.

26. The formulation of claim 1, for use in hemostasis, healing and/or surgery.

27. A container comprising the formulation of claim 1.

28. A kit comprising the container of claim 27, and optionally instructions for use.

29. A storage stable liquid sealant formulation comprising about 1-100 mg/ml fibrinogen; vitamin K-dependent clotting zymogens comprising at least Factor II, Factor IX and Factor X and having a ratio of about 0.01-1.0 IU/mg relative to fibrinogen; and at least one reversible inhibitor of at least one of the vitamin K-dependent clotting zymogens, wherein the formulation is free of added irreversible thrombin inhibitor; wherein the added reversible inhibitor is selected from the group consisting of 0.125 IU/ml heparin, about 1-50 mM calcium chelator, about 0.1-5% serine protease active site inhibitor and a combination thereof.

30. A storage stable liquid calcium-free sealant formulation comprising about 1-100 mg/ml fibrinogen and vitamin K-dependent clotting zymogens comprising at least Factor II and Factor X and having a ratio of about 0.01-1.0 IU/mg relative to fibrinogen, and at least one reversible inhibitor of at least one of the vitamin K-dependent clotting zymogens selected from the group consisting of 0.125 IU/ml heparin, about 1-50 mM calcium chelator, about 0.1-5% serine protease active site inhibitor and a combination thereof.

31. A container comprising the formulation of claim 29 or 30.

32. A kit comprising the container of claim 31; and optionally instructions for use.

\* \* \* \* \*